(12) United States Patent
Ercoli

(10) Patent No.: US 6,217,333 B1
(45) Date of Patent: Apr. 17, 2001

(54) DENTAL IMPLANT FOR PROMOTING REDUCED INTERPOXIMAL RESORPTION

(76) Inventor: Carlo Ercoli, 115 Running Brook La., Rochester, NY (US) 14626

( * ) Notice: Subject to any disclaimer, the term of this patent is extended or adjusted under 35 U.S.C. 154(b) by 0 days.

(21) Appl. No.: 09/566,715

(22) Filed: May 9, 2000

(51) Int. Cl.$^7$ ..................................................... A61C 8/00
(52) U.S. Cl. ........................ 433/173; 433/174; 433/201.1
(58) Field of Search ..................................... 433/172, 173, 433/174, 175, 176, 201.1

(56) References Cited

U.S. PATENT DOCUMENTS

| | | | |
|---|---|---|---|
| 5,362,236 | * 11/1994 | Branemark | 433/173 |
| 5,727,942 | * 3/1998 | Hartmann et al. | 433/173 |
| 5,759,034 | * 6/1998 | Daftary | 433/173 |

OTHER PUBLICATIONS

Weber et al., Comparison of healed tissues adjacent to submerged and non–submerged unloaded titanium dental implants; Clinical Oral Implants Research, 1996; pp. 11–19.

Ericsson et al. Radiographical and histological characteristics of submerged and nonsubmerged titanium implants; Clinical Oral Implants Research, 1996; pp. 20–26.

Persson et al. Bacterial colonization on internal surfaces of Branemark system implant components; Clinical Oral Implants Research, 1996; pp. 90–95.

Hammerle, et al. The effect of subcrestal placement of the polished surface of ITI implants on marginal soft and hard tissues; Clinical Oral Implants Research, 1996; pp. 111–119.

Malevez, et al. Marginal bone levels at Branemark system implants used for single tooth restoration. The influence of implant design and anatomical region. Clinical Oral Implants Research, 1996; pp. 162–169.

Bengazi, et al. Recession of soft tissue at oral implants; Clinical Oral Implants Research, 1996; pp. 303.

Abrahamsson, et al. The peri–implant hard and soft tissues at different implant systems. Clinical Oral Implants Research, 1996; pp. 212–219.

Hermann, et al. Crestal Bone Changes Around Titanium Implants. A Radiographic Evaluation of Unloaded Nonsubmerged and Submerged Implants in the Canine Mandible. Dept. of Periodontics, Dental School, University of Texas Health Science Center, San Antonio, TX; pp. 1117–1130.

Jansen et al. Microbial Leakage and Marginal Fit of the Implant–Abutment Interface. The Internatinal Journal of Oral & Maxillofacial Implants, vol. 12, No. 4, 1997; pp. 528–540.

Levy et al. A Comparison of Radiographic Bone Height and Probing Attachment Level Measurements Adjacent to Porous–Coated Dental Implants in Humans. The International Journal of Oral and Maxillofacial Implants, vol. 12, No. 4, 1997; pp. 541–546.

Buser et al. Soft Tissue Reactions to Non–Submerged Unloaded Titanium Imlants in Beagle Dogs. Journal of Periodontal, Mar. 1992; pp. 225–235.

(List continued on next page.)

*Primary Examiner*—Nicholas D. Lucchesi
(74) *Attorney, Agent, or Firm*—Harter, Secrest & Emery LLP; Stephen B. Salai, Esq.; Brian B. Shaw, Esq.

(57) ABSTRACT

A dental implant includes a generally longitudinal body having a first portion for receiving an artificial tooth and a second portion for engaging the hard tissue of a person receiving the implant, the second portion having coronal end adjacent the first portion, and a apical end, and a surface characterized by a texture compatible with osseointegration of hard tissue with the second portion, the second portion having a contour adjacent its coronal end having a generally saddle shaped configuration so that upon implantation, the surface of the second portion extends further from the apical end between adjacent teeth than it does in front or behind the artificial tooth.

16 Claims, 1 Drawing Sheet

OTHER PUBLICATIONS

Cochran et al. Biologic Width Around Titanium Implants. A Histometric Analysis of the Implanto–Gingival Junction Around Unloaded and Loaded Nonsubmerged Implants in the Canine Mandible. Journal of Periodontal, vol. 68, No. 2; pp. 186–197.

Fiorellini, et al. A Radiographic Evaluation of Bone Healing Around Submerged and Non–Submerged Dental Implants in Beagle Dogs. Journal of Periodontal, vol. 70, No. 3, Mar. 1999, pp. 248–254.

Pham et al. Longitudinal Radiographic Study of Crestal Bone Levels Adjacent to Non–submerged Dental Implants. Journal of Oral Implantology, vol. XX, No. 1, 1994; pp. 26–34.

Chaytor, et al. Clinical Criteria for Determining Implant Success: Bone. The International Journal of Prosthodonitcs, vol. 6, No. 22, 1993; pp. 145–152.

Weber et al. The Soft Tissue responde to Osseointegrated Dental Implants. The Journal of Prosthetic Dentistry, vol. 79, No. 1, 1998; pp. 79–89.

Ericsson et al. Different Types of Inflammatory Reactions in Peri–implant Soft Tissues. Journal of Clinical Periodontology. 1995; pp. 255–261.

Quirynen et al. Fixture Design and Oerlaod Influence Marginal Bone Loss and Fixture Success in the Branemark System. 1992; pp. 104–111.

Berglundh et al. The Soft Tissue Barrier at Implants and Teeth. Dept. of Periodontology, University of Gothenburg, 1991; pp. 81–90.

Naert, et al. Bone Behavior Around Sleeping and Non–sleeping Implants Retaining a Mandibular Hinging Overdenture. Clinical Oral Implants Research, vol. 10, 1999; pp. 149–154.

Al–Sayyed et al. Predictable Crestal Bone Remodelling Around Two Porous–Coated Titanium Alloy Dental Implant Designs. Clinical Oral Implants Research, vol. 5, 1994; pp. 131–141.

Esposito, et al. Radiological Evaluation of Marginal Bone Loss at Tooth Surfaces Facing Single Branemark Implants. Clinical Oral Implants Research; 1993 vol. 4, pp. 151–157.

Bragger et al. Evaluation of Postsurgical Crestal Bone Levels Adjacent to Non–submerged Dental Implants. Clinical Oral Implants Research; 1998, vol. 9; pp. 218.224.

* cited by examiner

DENTAL IMPLANT FOR PROMOTING REDUCED INTERPOXIMAL RESORPTION

BACKGROUND OF THE INVENTION

This invention relates generally to dental implants and more particularly to a dental implant having an improved configuration for reducing interproximal bone resorption compared with known implants.

Artificial dental implants, usually made of metal or ceramic, can be used in place of natural teeth to provide a base/support on which an artificial tooth can be fabricated. An artificial dental implant is implanted in the hard tissue (bone) of a patient (referred to as implant). The implant is composed of a machined/polished collar (coronal part) (referred to as collar) and an apical surface characterized by macroscopic and microscopic surface features (referred to as root). A mounting part (abutment) is attached to the implant (referred to as post) to which an artificial tooth (referred to as prosthesis; i.e. crown, denture etc.) can be attached.

Artificial dental implants of the type to which this invention relates can be made from metals, such as titanium and titanium alloys, as well as ceramics such as zirconia based, alumina-based, and sapphire based ceramics.

Of these materials, titanium and its alloys are the most widely used because of their fracture and fatigue resistance, corrosion resistance and biocompatibility.

While osseointegration can be obtained with different types of dental implants, it is common to observe bone loss around the implant in the first year of implant life. Bone loss up to 1 mm is considered to be acceptable in the first year, and bone loss no more than 0.1–0.2 mm is acceptable in subsequent years. Usually, after some initial bone loss, bone levels near the top of the implant (crestal bone level at the coronal macro-microscopic features) reaching a steady state and no significant further bone loss occurs.

A number of explanations for the greater bone loss in the first year after implantation have been proposed. Among these are remodeling of the bone crest due to mechanical loading of the implant, crestal remodeling due to abutment micro movement, crestal remodeling due to contact of polished and/or machined surface of the implant with bone, and resorption of the bone crest due to the presence of inflammatory infiltrate at the level of the implant-abutment junction, possibly caused by bacterial colonization of the inner surfaces of the implant.

Implants are generally cylindrical or modifications of cylindrical in form. The artificial tooth mounting surface (referred to as implant-abutment interface) is normally flat and arranged at an angle perpendicular to the long axis of the cylindrical implant. Conventionally, a machined and/or polished metal collar is immediately adjacent (in the apical direction) the artificial tooth mounting surface. In other words, the machined/polished collar is the most coronal portion of the implant (not considering the antirotational features that may be present at the implant-abutment interface) The collar may have a width of up to a few millimeters, depending on design choices made by the manufacturer.

The root of the dental implant can be threaded, serrated, or lack macroscopic surface features (press-fit design). At a microscopic level, some implant designs include surface modifications such as coating, etching, and grit-blasting to improve osseointegration.

Human tissues, including soft tissues (gums or gingiva) and hard tissues (bone), react differently to the different surfaces. Epithelial tissue (gum) can establish a stable attachment with the machined/polished collar. This attachment forms a seal against bacterial invasion of the underlying hard tissue (bone). Hard tissue that comes in contact with a machined or polished surface such as the surface of the collar is normally resorbed. Resorption normally progresses to and stop at the most coronal macro/microscopic surface features. Therefore, a longer polished/machined collar in contact with bone, leads to greater resorption.

In a healthy patient, the outline of the alveolar bone crest is curved. The outline follows the concavities and convexities of the cemento-enamel junction of the healthy tooth.

The free gingiva, junctional epithelium and connective tissue attachment to the tooth are the most coronal portion of the periodontum (tooth supporting apparatus). The apico-coronal dimension of the junctional epithelium and the connective tissue attachment are together defined as the biologic width. In healthy patients, the apico-coronal dimension of the biologic width is generally constant for different teeth, different individuals, and different ages. This dimension is also recreated during the healing process following periodontal surgery. Therefore, the dimension of the soft tissue (gums of gingiva) is generally constant. The dimension of the biologic width around dental implants and healthy natural teeth is similar. Moreover, different types of dental implants show similar biologic width dimensions.

Studies of implants several years after insertion show that resorption proceeds until the bone crest is at the level of the most coronal macroscopic feature (the first thread for a machined threaded design or serration) or to the level of the most coronal part of the surface microscopic features (coating, etching, and grit-blasted surface). Since, heretofore, the macroscopic and microscopic features lie in a flat line perpendicular to the long axis of the implant, bone loss proceeds to the same level all the way around the implant, including the mesial, buccal, distal, and lingual surfaces. Because the bone level around a natural tooth is not flat, more resorption of the interproximal bone peak occurs than of the buccal and lingual portions. The loss of bone, particularly of the interproximal bone peak, often leads to apical migration of the overlying soft tissues (that have constant dimension: biologic width), including the connective tissue and epithelium, with a resultant gingival recession. This loss is particularly accentuated in the interproximal areas, that are the sides that face another tooth or implant, and is particularly severe when two implants are placed side by side. Gingival recession can lead to an unsightly gap between an implant-supported artificial tooth and an adjacent natural tooth or another implant-supported artificial tooth.

It is an object of this invention to provide an improved dental implant that decreases or eliminates interproximal bone loss by providing an implant that has a coronal part that is curved or angled to correspond to or imitate the cemento-enamel junction of a natural tooth.

It is another object of this invention to provide a dental implant having a polished and/or machined collar and macro/microscopic surface feature that are more coronally extended in the interproximal areas of the implant as mounted in a patient.

It is yet another aspect of this invention to provide an implant having a curved or otherwise angled outline of the coronal machined/polished metal collar that also follows the outline of the cemento-enamel junction and the alveolar bone crest.

It is still another aspect of this invention to provide a dental implant having macroscopic and microscopic surface features that follow the outline of the machined collar.

BRIEF DESCRIPTION OF THE DRAWINGS

The novel aspects of the invention are set forth with particularity in the appended claims. The invention itself, together with further objects and advantages thereof may be more readily comprehended by reference to the following detailed description of a presently preferred embodiment of the invention taken in conjunction with the accompanying drawing, in which:

DETAILED DESCRIPTION OF THE PREFERRED EMBODIMENT OF THE INVENTION

Figure 1:
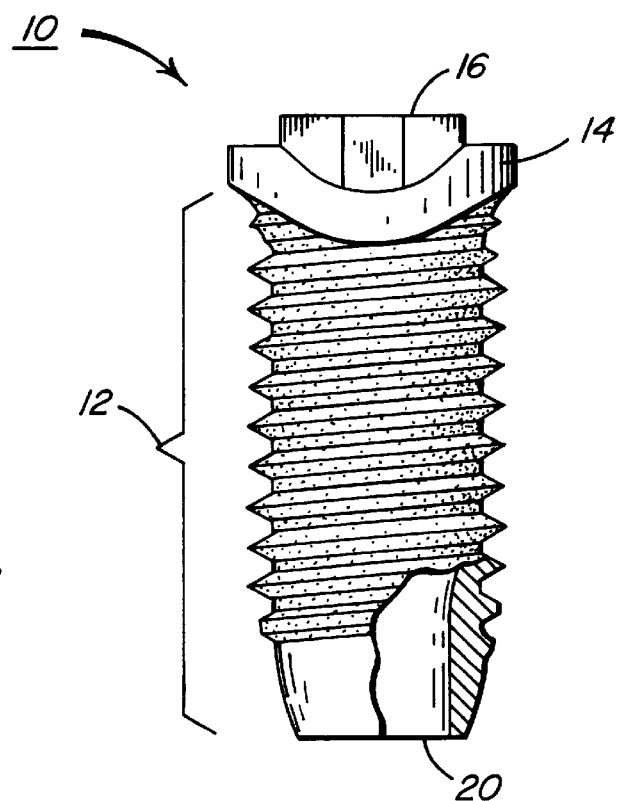
FIG. 1 is a front view of a dental implant in accordance with this invention; (seen from buccal or lingual sides)

Dental implant 10 has three functional parts, a root part 12, a coronal part (collar) 14, and an artificial tooth attaching part 16. For convenience, and to afford a consistent frame of reference for an implant that may be implanted in a variety of positions and orientations, the implant 10 will be referred to using the terms that are used to refer to a natural tooth located in the same position and orientation. That is, the implant will be considered as having four surfaces (even though it is essentially round), a buccal surface, a lingual surface, a mesial proximal surface, and a distal proximal surface. The end of the implant that is intended to be anchored in the jaw is the apical end, and the end to which an artificial tooth or the like is to be attached is the coronal end. These terms are position and orientation independent, and provide a convenient way to refer to the parts of the implant of this invention, which is intended to be implanted with the named surfaces oriented in the same way as the like named surfaces of a natural tooth.

The root part 12, which may also be referred to as an implanting part, is designed, and constructed for anchoring in the hard tissue (bone) of a patient. Typically, a hole slightly smaller than the outside diameter of the implant is formed in a patient's jaw and the implant is inserted into the hole. Alternatively, a hole of the same diameter as of the implant can be made, tapped, and the implant inserted. The implant part 12 (root) can be generally cylindrical, or tapered, or any other shape adapted to achieve osseointegration with the hard tissue. Known shapes such as cylindrical, tapered, stepped cylindrical and blade shapes, among others, may be employed in the dental implants in accordance with this invention. The invention is not intended to be limited to any one shape.

The implant part root 12 extends from a apical end 20 of the implant 10 to the apical portion of coronal part 14.

Coronal part 14 preferably has a smooth machined surface adapted to enhance a stable attachment of epithelial tissue. The coronal part 14 is sometimes referred to as a collar.

Tooth attaching part 16 is located at the coronal end of the implant. Attaching part 16, when a crown or other prosthesis are fabricated on the implant, does not ordinarily come into contact with live tissue, and its primary function is to provide the attachment of an artificial tooth, crown, bridge, or similar array of teeth or a single tooth. Typically, a threaded recess is provided for attaching a post to attaching part 16 on which post an artificial tooth or the like can be mounted.

The surface of the implant part 12 may take a variety of forms. The implant shown in FIGS. 1 and 2 has a threaded implant portion, particularly designed to be screwed in place into a patient's hard tissue. Preferably, in addition to threads, the surface of the implant portion 12 is slightly roughened by grit-blasting, etching, coating or the like. A rough surface promotes better and faster attachment of hard tissue and reduces resorption. While threaded implant portions are preferred, other arrangements (press-fit design) may also be utilized in an implant according to this invention. This invention is intended to include any macroscopic surface design, threaded and press-fit designs, as well as any microscopic treatment such as machining, grit-blasting, etching and coating, which promotes bone attachments.

Figure 2:
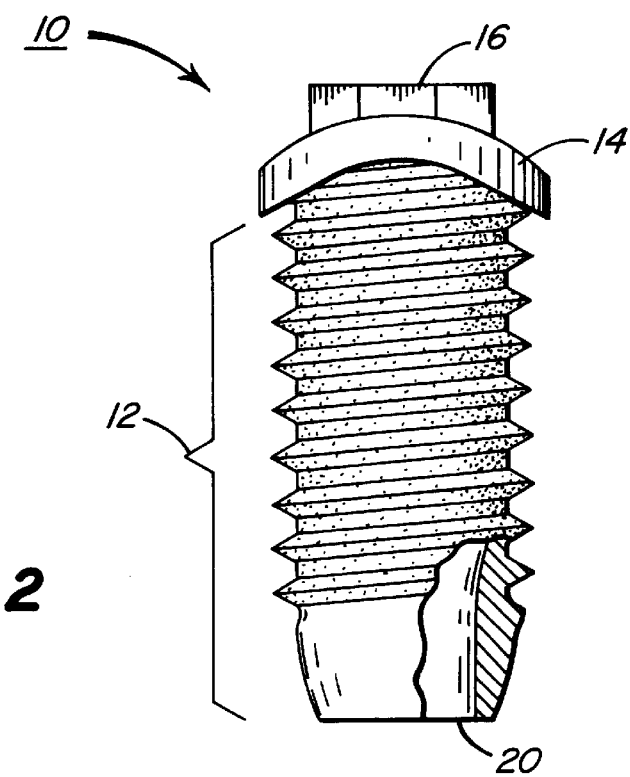
FIG. 2 is a side view of the dental implant of FIG. 1 (seen from interproximal [mesial or distal] sides).

As shown in FIG. 1, the collar 14 has an undulating shape. Referring first to FIG. 1, this figure shows what would be, if the implant were a tooth, the buccal surface facing forward, that is out of the page. The lingual surface, not shown, would be identical (opposite surface). FIG. 2 shows what would, if the implant were a tooth, be the mesial proximal surface, the distal proximal surface being a mirror image. As can be readily seen from the two figures, the collar 14 has a peak at the center of the distal proximal and mesial proximal surfaces, and a valley at the center of the buccal and lingual surfaces.

The upper edge of the attachment part 12 follows the distal and mesial contour of the collar 14. That is, the attaching part 12 has peaks at the center of the distal proximal and mesial proximal surfaces and valleys at the centers of the buccal and lingual surfaces.

It will be understood that to the extent that the words peak and valley convey the sense of higher and lower, these senses are reversed when the implants shown in FIGS. 1 and 2 are installed in the upper jaw of a patient. Therefore, for clarity, it will be understood that peaks and valleys are terms used with respect to the insert without regard to the orientation of the insert when actually implanted in a patient.

By shaping collar 14 in the manner just described, the coronal end of the bone-attachment-promoting surface of the root portion 12 also has an irregular shape. Specifically, the surface is longer (measured from the apical end) in the centers of the distal proximal and mesial proximal surfaces and shorter, measured from the apical end, in the centers of the buccal and lingual surfaces.

When an implant as described is placed in the hard tissue of a patient, namely anchored in a jaw bone, the extended bone attachment surface, at the mesial proximal and distal proximal portions of the implant, reduces resorption of hard tissue in the regions between the implant and an adjacent tooth or between adjacent implants by providing an extended surface with characteristics that promote hard tissue attachment. Reducing bone resorption reduces gingival recession. Therefore, when an implant in accordance with this invention is used, soft tissue recession between teeth is reduced, and gaps between teeth which have been a problem up to now, are substantially reduced or eliminated. The apical end of the curved or otherwise angle collar is generally aligned with the residual bone. If placed more coronal, graft material may be used to augment the bone in the interproximal areas.

While the invention has been described in conjunction with a presently preferred embodiment thereof, those skilled in the art will recognize that certain modifications and changes may be made therein without departing from the true spirit and scope of the invention. For example, while the coronal collar is shown having a gently curved configuration, and while such a configuration is preferred, a zig-zag (angled) configuration could be employed to achieve substantially similar benefits. Also, while the width of the collar is maintained substantially constant in accordance with presently preferred embodiment of the invention, some of the benefits of the invention would be provided by an insert having a collar with a substantially flat upper surface, and a lower surface as shown.

While the implant described has an external hex shaped tooth attaching portion, an internal hex or other suitable shaped tooth attaching portion can also be used without requiring any other significant change to the invention.

What is claimed is:

1. A dental implant comprising:
    a generally longitudinal body having a first portion for receiving an artificial tooth and a second portion for engaging the hard tissue of a person receiving the implant, the second portion having coronal end adjacent the first portion, and a apical end, and a surface characterized by a texture compatible with osseointegration of hard tissue with the second portion, the second portion having a contour adjacent its coronal end having a generally saddle shaped configuration so that upon implantation, the surface of the second portion extends further from the apical end between adjacent teeth than it does in front or behind the artificial tooth.

2. A dental implant having a tooth attaching part for receiving an artificial tooth, and a root that is adapted to be placed into a hole drilled in a patients jaw, to replace the root of a tooth, the root of the implant having a surface texture that promotes attachment of bone tissue of the jaw to the surface of the implant, the surface extending from one end (apical) of the implant towards the tooth attaching part and having a contoured shape that promotes additional bone attachment between the teeth, and less attachment in front of and behind the teeth, to simulate natural greater bone growth between the teeth.

3. A dental implant having a tooth attaching coronal end and an apical end for implanting in hard tissue of a patient, and buccal, lingual, mesial proximal, and distal proximal surfaces, comprising:
    a hard tissue receptive surface extending from an apical end of the implant towards a coronal end, the hard tissue receptive surface on at least one of the distal proximal, and mesial proximal surfaces being longer than the hard tissue receptive surface on at least one of the buccal and lingual surfaces.

4. The dental implant of claim 3 in which the hard tissue receptive surface comprises microscopic surface features for promoting hard tissue attachment, and/or reducing resorption.

5. The dental implant of claim 4 in which the hard tissue receptive surface is rough.

6. The dental implant of claim 5 in which the hard tissue receptive surface is etched.

7. The dental implant of claim 5 in which the hard tissue receptive surface is grit-blasted.

8. The dental implant of claim 5 in which the hard tissue receptive surface is coated with a bone receptive coating.

9. The dental implant of claim 3 in which the hard tissue receptive surface comprises macroscopic surface features for promoting hard tissue attachment, and/or educing resorption.

10. The dental implant of claim 9 in which the hard tissue receptive surface is threaded.

11. The dental implant of claim 9 in which the hard tissue receptive surface is a stepped conical surface.

12. The dental implant of claim 3 comprising a collar adjacent a coronal end of the implant.

13. The dental implant of claim 12 in which the collar has a smooth surface.

14. The dental implant of claim 12 in which the collar extends further towards the apical end of the implant at the buccal and lingual surfaces that at the distal proximal and mesial proximal surfaces.

15. The dental implant of claim 14 in which the collar has a substantially constant width, measured from the apical end of the implant towards the coronal end thereof.

16. The dental implant of claim 12 comprising a tooth mounting part at the coronal end.

* * * * *